United States Patent [19]

Russell-Jones et al.

[11] Patent Number: 5,548,064
[45] Date of Patent: Aug. 20, 1996

[54] VITAMIN B12 CONJUGATES WITH EPO, ANALOGUES THEREOF AND PHARMACEUTICAL COMPOSITIONS

[75] Inventors: Gregory J. Russell-Jones, Middle Cove; Steven W. Westwood, Ashfield, both of Australia

[73] Assignee: Biotech Australia Pty Limited, Roseville, Australia

[21] Appl. No.: 64,873

[22] Filed: May 24, 1993

[51] Int. Cl.$^6$ .................. C07H 23/00; C07K 2/00
[52] U.S. Cl. ............... 530/380; 530/399; 536/26.4; 536/26.41
[58] Field of Search ............... 514/12; 930/90, 930/351; 530/380, 399; 536/26.4, 26.41

[56] References Cited

U.S. PATENT DOCUMENTS

| | | | |
|---|---|---|---|
| 3,876,765 | 4/1975 | Choay | 424/105 |
| 3,962,416 | 6/1976 | Katzen | 424/19 |
| 4,007,266 | 2/1977 | Choay | 424/105 |
| 4,235,869 | 11/1980 | Schwartzberg | 424/8 |
| 4,672,040 | 6/1987 | Josephson | 436/526 |
| 4,677,195 | 6/1987 | Hewick et al. | 530/397 |
| 4,732,889 | 3/1988 | Cynshi et al. | 514/8 |
| 4,745,099 | 5/1988 | Akamatsu et al. | 514/8 |
| 4,963,367 | 10/1990 | Ecanow | 424/485 |
| 5,026,826 | 6/1991 | Evans et al. | 530/351 |
| 5,071,834 | 12/1991 | Burton et al. | 514/12 |
| 5,162,430 | 11/1992 | Rhee et al | 525/54.1 |
| 5,206,219 | 4/1993 | Desai | 514/3 |
| 5,292,802 | 3/1994 | Rhee et al. | 525/54.1 |
| 5,308,889 | 5/1994 | Rhee et al | 523/113 |

FOREIGN PATENT DOCUMENTS

| | | | |
|---|---|---|---|
| 0513738 | 11/1992 | European Pat. Off. | C12N 5/00 |
| 2546474 | 4/1977 | Germany . | |
| WO87/02251 | 4/1987 | WIPO . | |
| 9325221 | 12/1993 | WIPO . | |
| 9325583 | 12/1993 | WIPO | C07K 15/00 |
| 9324154 | 12/1993 | WIPO | A61L 15/62 |
| 9401483 | 1/1994 | WIPO | C08G 63/48 |

OTHER PUBLICATIONS

Chan et al., "Pharmacokinetics and Metabolism of LHRH Analogs," Ch. 37 in *LHRH and Its Analogs; Contraception and Therapeutic Applications Part 2*, Vickery & Nestor eds., Kluwer Academic Publishers, Norwell, MA, 1987, pp. 577–593.

Kwan et al., "Biopharmaceutics," Ch. 9 in *The Theory and Practice of Industrial Pharmacy*, Lochman, Lieberman & Kanig eds., Williams and Wilkins, 1986, pp. 197–242.

deKlerk et al., "Serum Erythropoietin (ESF) Titers in Anemia." *Blood*, 58(6), 1164–1170 (1981).

Neiman et al., "Carcinogenic Agents and Reactions of Organism in Response to Them," Patol. Fiziol. Eksp. Ter., 1972(4), 14–18; *Chem. Abstr.*, 77(25), p. 73, Abstr. No. 160683t (1972); only Abstract supplied.

Babior (ed.), *Cobalamin–Biochemistry and Pathophysiology*, Wiley–Interscience, New York, 1975, p. 25.

Anton et al. "Carbon–13 Nuclear Magnetic Resonance Studies of the Monocarboxylic Acids of Cyanocobalamin. Assignments of the b—, d—, and e—Monocarboxylic Acids," *J. Am. Chem. Soc.* 102: 2215–2219 (1980).

Rejmanová et al. "Polymers Containing Enzymatically Degradable Bonds, 2 Poly [N–(2–hydroxypropyl)methacrylamide]Chains Connected by Oligopeptide sequences. . . ," *Makromol. Chem.* 182: 1899–1915 (1981).

Primary Examiner—Douglas W. Robinson
Assistant Examiner—L. Eric Crane
Attorney, Agent, or Firm—Foley & Lardner

[57] ABSTRACT

The invention describes complexes between $VB_{12}$ analogues and either GCSF or EPO that retain both significant affinity for intrinsic factor (IF) in the $VB_{12}$ portion of the complex and significant bioactivity of the GCSF or EPO portion of the complex. The invention also concerns a process for the synthesis of these complexes. This is achieved at least in part, by using a spacer compound, which is linked covalently between the $VB_{12}$ portion and the GCSF or EPO. The complexes preferably have the formula $$V-X-A-Y-Z$$

wherein

V is vitamin $B_{12}$ or a vitamin $B_{12}$ analogue, or derivative, bonded to X either through a carboxylate group pendant to the corrin nucleus of $VB_{12}$ or through the central cobalt atom or to a functional group introduced onto the $VB_{12}$ molecule, X is selected from: —NHNH—, —NH—, —O—, —S—, —SS— or —CH$_2$—, and A is an optionally substituted, saturated or unsaturated, branched or linear, $C_{1-50}$ alkylene, cycloalkylene or aromatic group, optionally with one or more carbons within the linear chain being replaced with N, O or S, and wherein the optional substituents are selected from carbonyl, carboxy, hydroxy, amino and other groups, and Y is the covalent linkage between A and Z where Y is selected from —NHCO—, —CONH—, —CONHNHCO—, —N=N—, —N=CH—, —NHCH$_2$—, —NHN=CH—, —NHNHCH$_2$—, —SS—, —SCH$_2$—, —CH$_2$S—, —NHCRNH—, —COO—, —OCO—, and R is O, S or NH$_2$, and Z is GCSF or EPO. The invention also describes reagents that can be used as probes for the detection of buried thiol groups of a protein or peptide, said reagent comprising a complex of either vitamin $B_{12}$ (or an analogue thereof) or more generally of any instrumentally or visually detectable label, covalently linked to a diradical spacer, said spacer having a terminal reactive group capable of forming a disulphide bond with a free thiol in said protein or peptides.

9 Claims, No Drawings

VITAMIN B12 CONJUGATES WITH EPO, ANALOGUES THEREOF AND PHARMACEUTICAL COMPOSITIONS

BACKGROUND OF THE INVENTION

The present invention relates to the oral delivery of the therapeutic substances granulocyte-colony stimulating factor (GCSF) and erythropoietin (EPO) by administration of a complex comprising these substances linked to vitamin $B_{12}$ ($VB_{12}$) or an analogue thereof. More particularly, the invention relates to methods for the synthesis of these complexes and to methods for the amplification of the amount of GCSF or EPO delivered per $VB_2$ carrier molecule.

An oral delivery system is known, because of recent work undertaken by one of the current inventors, which is described in PCT Application WO87/02251 (PCT/AU86/0299), whereby an active substance linked to at least one carrier molecule, which is $VB_{12}$ or an analogue thereof, can use the natural $VB_{12}$ uptake system mediated by the binding of $VB_{12}$ to intrinsic factor (IF) to transport the resultant complex from the intestinal lumen into the circulation. Once delivered into serum or the lymphatic drainage system the complex substantially retains the bioactivity of the native active substance.

In common with virtually all proteins, peptides and other large bioactive molecules there is currently no method for the oral delivery of either GCSF or EPO. The oral route of administration is the most preferable means of delivering a pharmaceutically active agent, and as such there is a large and valuable market for any process which permits the oral delivery of either of these proteins to humans. Such a process would be available by the formation of a complex between $VB_{12}$ and GCSF or EPO.

SUMMARY OF THE INVENTION

It is thus the object of the invention to describe complexes between $VB_{12}$ analogues and either GCSF or EPO that retain both significant affinity for intrinsic factor (IF) in the $VB_{12}$ portion of the complex and significant bioactivity of the GCSF or EPO portion of the complex. The invention also concerns a process for the synthesis of these complexes. This may be achieved at least in part, by using a spacer compound, which is linked covalantly between the $VB_{12}$ portion and the GCSF or EPO.

DESCRIPTION OF THE PREFERRED EMBODIMENTS

One aspect of the invention provides a complex which comprises at least one active substance linked to at least one carrier molecule, which is $VB_{12}$ or an analogue of $VB_{12}$ wherein the ability of the carrier to undergo the binding reactions necessary for uptake and transport of $VB_{12}$ in a vertebrate host and the activity of the active substance are substantially maintained. This occurs by providing a complex between GCSF and a carrier selected from vitamin $B_{12}$ or a vitamin $B_{12}$ analogue wherein the GCSF and the carrier are covalently linked through a diradical spacer, the complex being capable of binding to intrinsic factor with high affinity with maintenance of GCSF bioactivity.

The complex preferably has the general form V—X—A—Y—Z, where V is the carder molecule $VB_{12}$ or an analogue (including derivatives) thereof that retains IF affinity, Z is the active substance selected from EPO or GCSF, A is a spacer arm of variable composition and length, X is the functional group through which V is attached to A, and Y is the functional group through which Z is attached to A. The nature of functional group X, its site of attachment to V and the nature of spacer arm A are chosen to maximise the IF affinity of the complex. The nature of functional group Y, its site of attachment to Z and the nature of spacer arm A are chosen to maintain substantially the bioactivity of Z.

Preferably X is selected from: —NHNH—, —NH—, —O—, S—, —SS— or —CH$_2$—. A is preferably an optionally substituted, saturated or unsaturated, branched or linear, $C_{1-50}$ alkylene, cycloalkylene or aromatic group, optionally with one or more carbons within the linear chain being replaced with N, O or S, and wherein the optional substituents are selected from carbonyl, carboxy, hydroxy, amino and other groups. Y is preferably a covalent linkage between spacer chain A and protein Z, where Y is selected from —NHCO—, —CONH—, —CONHNHCO—, —N=N, —N=CH—, NHCH$_2$, —NHN=CH—, —NHNHCH$_2$, —SS—, —SCH$_2$—, —CH$_2$S—, —NHCRNH— [where R=O, S or NH$_2$], —COO—, —OCO—, and Z is GCSF or EPO.

In the context of the present invention, the term "active substance" (ie Z) includes all, part, an analogue, homologue, derivative or combination thereof of either granulocyte colony stimulating factor (GCSF) or erythropoietin (EPO).

The carrier is $VB_{12}$ or $VB_{12}$ analogue. The $VB_{12}$ analogues include any variant or derivative of $VB_{12}$ (cyanocobalamin) which possesses binding activity to intrinsic factor. Preferred analogues of $VB_{12}$ also include aquocobalamin, adenosylcobalamin, methylcobalamin, hydroxycobalamin, cyanocobalamin, carbanalide, and 5-methoxybenzylcyanocobalamin ([( 5-MeO)CN-Cbl] as well as the desdimethyl, monoethylamide and the methylamide analogues of all of the above. Other analogues include all alkyl cobalamins in which the alkyl chain is linked to the corrin nucleus by a direct CoC covalent bond. Other analogues include chlorocobalamin, sulfitocobalamin, nitrocobalamin, thiocyanatocobalamin, benzimidazolecyanocobalamin derivatives such as the: 5,6-dichlorobenzimidazole, 5-hydroxybenzimidazole, trimethylbenzimidazole, as well as adenosylcyanocobalamin [(Ade)CN-Cbl], cobalamin lactone, cobalamin lactam and the anilide, ethylamide, monocarboxylic and dicarboxylic acid derivatives of $VB_{12}$ or its analogues.

Preferred derivatives of $VB_{12}$ also include the mono-, di- and tricarboxylic acid derivatives or the propionamide derivatives of $VB_{12}$. Carriers may also include analogues of $VB_{12}$ in which the cobalt is replaced by zinc or nickel. The corrin ring of $VB_{12}$ or its analogues may also be substituted with any substituent which does not effect its binding to IF, and such derivatives of $VB_{12}$ or its analogues are pan of this invention. Other derivatives of $VB_{12}$ or its analogues which have a functional group which is able to react with the spacer compound are also part of the invention.

It is preferred that the complex may comprise GCSF linked through a disulphide bond to a (dithiopyridyl propionamido) dodecylamino [DTP-dodecylamino] derivative of $VB_{12}$.

Another preferred embodiment of the invention provides a process for the production of a complex comprising GCSF linked through a disulphide bond to a (dithiopyridyl propionamido) dodecylsuberylhexylamino derivative of $VB_{12}$, (a long-chain analogue of the DTP-dodecylamino $VB_{12}$) which displays higher affinity for intrinsic factor.

Another preferred embodiment of the invention provides a process for the production of a complex comprising GCSF linked through a disulphide bond to an (dithiopyridyl propionamido) dodecylcarboxamidomethyl derivative of $VB_{12}$, in which the spacer is linked to the $VB_{12}$ through an axial CoC bond.

Another embodiment of the invention provides a process for the production of a complex comprising at least one active substance linked to at least one carrier molecule through a spacer, the carrier molecule being $VB_{12}$ or an analogue thereof, wherein the ability of the carrier to undergo the binding reactions necessary for uptake and transport of $VB_{12}$ in a vertebrate host and the activity of the active substance are substantially maintained, the process comprising one or more of the following steps:

a) reacting together the active substance and the carrier and the spacer compound to form the complex;

b) reacting the active substance with the spacer, and then reacting the product with the carrier to form the complex;

c) reacting the carrier with the spacer, and then reacting the product with the active substance to form the complex;

d) following method of (a), (b) or (c) but with the additional step of having chemically modified the carrier and/or the active substance in a previous step to provide a functional group on the carrier and/or active substance which will react with the spacer compound; or e) following the method of (a), (b), (c) or (d) but with the additional step of reacting the active substance or the carrier with a polymeric support, before carrying out the further reactions. Preferably the polymeric support is bonded both to the carrier (or spacer carrier), and also to the active substance or (spacer-active substance).

For example, it is possible to form these complexes using the "e" mono -acid of "e"$VB_{12}$ by: (i) preparing the mono-acid derivative of $VB_{12}$ by mild acid hydrolysis of cyanocobalamin and purifying the initial hydrolysate; (ii) modifying the e-mono-acid to give a terminal functional group attached to the e$VB_{12}$ nucleus through a spacer arm; (iii) coupling the functionalised e$VB_{12}$ derivative to carboxylate, amine, thiol, hydroxyl, phenol, aldehyde or ketone groups or other suitable functional groups present initially or introduced chemically on the active substance. The spacer compound can be selected to have suitable functional groups at either end of its backbone, or else these functional groups can be introduced, if necessary by normal chemical synthetic reactions.

The invention also involves the modification of a polymeric support to introduce functional groups capable of reacting either directly with the spacer compound or with the spacer linked with the active substance. The resulting polymer-active substance intermediate ideally contains many molecules of the active substance, and this intermediate is suitable for coupling to the carrier to give a complex capable of amplified delivery of the active substance.

The invention also concerns a general method for the modification of unreactive thiols in peptides and proteins, particularly those not normally exposed to reagents dissolved in aqueous solvents because they are buried in hydrophobic regions of the protein. These modified peptides and proteins can then be labelled, if desired.

The invention also involves a reagent, of the general formula:

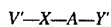

wherein, V' is vitamin $B_{12}$ or a vitamin $B_{12}$ analogue, bonded to X either through a carboxylate group pendant to the corrin nucleus of $VB_{12}$ or through the central cobalt atom or to a functional group introduced onto the $VB_{12}$ molecule, or V' is a label, where "label" refers to any substance that is detectable by visual or instrumental methods. Labels can include chromogens, catalysts, fluorescent compounds, chemiluminescent compounds, radioactive isotopes, colloidal metal and non-metallic particles, dye particles, enzymes or substrates, antibodies or antigens, biotin, avidin or streptavidin, latex particles, liposomes or other vesicles containing signal producing substances, and the like.

X is selected from —NHCO—, —CONH—, —CONHNHCO—, —N=N—, —N=CH—, —NHCH$_2$—, —NHN=CH—, —NHNHCH$_2$, —SS—, —SCH$_2$—, CH$_2$S—, —NHCRNH—, [R is O, S or NH$_2$], —COO—, —OCO—, and A is an optionally substituted, saturated or unsaturated, branched or linear, $C_{1-50}$ alkylene, cycloalkylene or aromatic group, optinally with one or more carbons within the chain being replaced with N, O or S, and wherein the optional substituents are selected from carbonyl, carboxy, hydroxy, amino and other groups, and Y' is a functional group capable of reacting with thiols to give a stable covalent linkage, including iodoacetyl, bromoacetyl, chloroacetyl, maleimido, 3-carboxy-4-nitrophenyldithio or 2-pyridyldithio, and similar groups.

BEST METHOD OF CARRYING OUT THE INVENTION

EXAMPLES

Materials: $VB_{12}$ was obtained from Rousell-Uclaf. GCSF and EPO were obtained from Amgen. 1-Ethyl-3-(dimethylaminopropyl) carbodiimide. HCl (EDAC.HCl) was obtained from Biorad. N-Succinimidyl 3-(2-pyridyldithio) propionate (SPDP) and succinimidyl, 6-[3-(2-pyridyldithio) propionamido] hexanoate (LC-SPDP) were obtained from Pierce Chemical Co. All other reagents were obtained from Fluka.

Example 1: $VB_{12}$ -GCSF complexes

Three classes of $VB_{12}$-GCSF complexes were prepared:
a) conjugated via an amide linkage, formed by carbodiimide (EDAC) mediated coupling of an amino terminal e$VB_{12}$ derivative to the C-terminus of GCSF or the carboxylate side chains of GCSF.

b) conjugated via a disulphide linkage formed by a thiol insertion reaction of the free thiol at Cys-17 of GCSF into the disulphide bond present in the (dithiopyridylpropionamido) terminal derivatives of e$VB_{12}$.

c) conjugated via an acyl hydrazide linkage, formed by EDAC-mediated coupling of a hydrazido-terminal e$VB_{12}$ derivative to the C-terminus of GCSF or the carboxylate side chains of GCSF.

1.1 Production and purification of the "e" isomer of monocarboxy-$VB_{12}$.

The "e" isomer of monocarboxy vitamin $B_{12}$, formerly named the d isomer, but reassigned by Anton and co-workers (1980: J. Am. Chem. Soc. 102:2215) as the e isomer, was separated from the b and d isomers formed during acid hydrolysis of cyanocobalamin by a combination of Dowex 1X2 chromatography and semi-preparative C-18 RP-HPLC developed with a gradient of acetonitrile in 0.1% TFA.

1.2 Production of amino-derivatives of e$VB_{12}$

A number of amino-derivatives of e$VB_{12}$ were prepared by reacting the e isomer with:
i) 1,2-diaminoethane
ii) 1,6-diaminohexane
iii) 1,12-diaminododecane
iv) 1,3-diamino-2-hydroxypropane v) 1,6-diamino-3,4-dithiahexane (a.k.a. cystamine)

All reactions were performed at pH 6.5 using a twenty fold molar excess of the diamine over e isomer and a twenty fold molar excess of EDAC. In a typical reaction 135 mg of $eVB_{12}$ was dissolved in distilled water (6 ml) to which was added 1.2 ml of 1.0M diamine, pH 6.5. Dry EDAC (270 mg) was then added and the reaction mixture was left overnight at room temperature.

All amino derivatives were purified by reverse phase chromatography on a semi-preparative C-4 column using a 5–100% acetonitrile gradient in 0.1% TFA. Eluted material was further purified by S-Sepharose chromatography. The amino-derivative was eluted with 0.1M HCl, followed by extraction into phenol, and back-extraction into water after the addition of dichloromethane to the phenol phase. The amino-$eVB_{12}$ derivatives were then recovered from the water phase by lyophilization.

1.3 Conjugation of 2-aminoethyl-$eVB_{12}$ to GCSF

A solution of 2-aminoethyl-$eVB_{12}$ (26.5 mg, 18 µmol) in 2 ml of GCSF (6 mg/ml, 0.63 µmol) was cooled to 4 C. An aliquot of freshly prepared EDAC solution (100 mg/ml, 120 µl, 63 µmol) was added. After 24 h at 4 C. a second aliquot of freshly prepared EDAC solution was added. The reaction was allowed to proceed for a total of 48 h at 4 C., after which the unreacted 2-aminoethyl-$eVB_{12}$ was separated from the conjugate and aggregate by chromatography on Sephadex G-50 in 2.5% acetic acid.

1.4 Conjugation of cystaminyl-$eVB_{12}$ to GCSF

A solution of cystaminyl-$eVB_{12}$ hydrochloride (30 mg, 20 µmol) in 2.5 ml of GCSF (6 mg/ml, 0.80 µmol) at 4 C. was treated with an aliquot of an aqueous EDAC solution (20 mg/ml, 75 µl, 8 µmol). Further aliquots of freshly prepared EDAC solution (20 mg/ml, 75 µl, 8 µmol) were added after 4.5 h, 7 h and 24 h. The reaction was allowed to proceed for a total of 48 h at 48 C., after which time the unreacted amino-$eVB_{12}$ was separated from the conjugate by chromatography on Sephadex G-S50 in 2.5% acetic acid.

1.5 Preparation of 3-(2-pyridyldithio) propionamido derivatives of aminoethyl-$eVB_{12}$ The dithiopyridyl derivatives of amino-$eVB_{12}$ were prepared by reacting SPDP with:

i) 2-aminoethyl-$eVB_{12}$
ii) 6-aminohexyl-$eVB_{12}$
iii) 12-aminododecyl-$eVB_{12}$ In a typical reaction the terminal amino-$eVB_{12}$ was dissolved at 50 mg/ml in 0.1M $PO_4$ buffer, pH 7.5, containing 0.1M NaCl. SPDP was dissolved at 50 mg/ml in acetone and 800 µl of the solution was added to the amino-$eVB_{12}$. After reaction overnight at room temperature the DTP-amino-$eVB_{12}$ was purified by RP-HPLC on a semi-prep C4 column, and then lyophilized.

1.6 Conjugation of DTP-amino-$VB_{12}$ to GCSF

In initial conversations with AMGEN it was revealed that they had found that it was impossible to modify the free cysteine in undenatured GCSF with standard thiol modifying agents. Initial experiments with DTP-aminoethyl-$eVB_{12}$ showed that it was possible to achieve some 20% substitution of GCSF with the $VB_{12}$ in the absence of guanidine; this level rose to >80% in the presence of 4M guanidine. It was therefore decided that it might be possible to access the free thiol with DTP-amino-$eVB_{12}$ in the absence of guanidine if a longer spacer was used for the conjugation.

In a second series of experiments GCSF was reacted with DTP-aminoethyl-, DTP-aminohexyl- and DTP aminododecyl-$eVB_{12}$ in the presence or absence of 4M guanidine in 0.1M sodium acetate buffer, pH 4.0.

The degree of substitution of GCSF by various DTP-amino-$eVB_{12}$-spacer complexes is shown in the following table:

TABLE 1

| Spacer | Guanidine | +Guanidine |
| --- | --- | --- |
| DTP-aminoethyl- | 37.5% | 89.3% |
| DTP-aminohexyl- | 45.5% | 95.2% |
| DTP-aminododecyl- | 100.0% | 100.0% |

From Table 1 it can be seen that by switching to the longer dodecyl-spacer it was possible to conjugate to the buried thiol in GCSF without the use of guanidine.

The initial attempts to conjugate to the free thiol group in GCSF using the pyridyldithiopropionamido-aminoethyl derivative of $eVB_{12}$ resulted in a small degree of conjugation, of around 20–40 percent in the absence of guanidine. The addition of 4M guanidine (final concentration) raised the conjugation efficiency to over 80%. Preparation of a longer, more hydrophobic derivative of $eVB_{12}$, pyridyldithiopropionamido-dodecyl $eVB_{12}$ resulted in 100% substitution of GCSF after 24 h at 4 C., without the need for the addition of guanidine. The use of the thiol interchange chemistry in this reaction proved advantageous as the $eVB_{12}$ conjugation was surprisingly successful at pH's which minimised the extent to which GCSF undergoes spontaneous aggregation. Chromatography of the conjugated material resulted in base-line separation of conjugate from free $eVB_{12}$.

This type of approach can be more generally applied for the development of reagents capable of detecting, quantifying and/or modifying thiol groups in proteins and peptides which were hitherto regarded as chemically unreactive.

1.7 Scale up conjugation of DTP-aminododecyl-$eVB_{12}$ to GCSF

Following the initial success with the conjugation of the DTP-dodecyl-spacer, the reaction was scaled up as follows:

To 2.5 ml of GCSF (6 mg/ml; 15 mg) was added 1.6 ml of DTP-aminododecyl-$eVB_{12}$ (10 mg/ml in 2.5% acetic acid). The reaction was allowed to proceed for 48 h at 4 C., after which the unreacted $eVB_{12}$ was separated from the conjugate by chromatography on Sephadex G-25 in 2.5% acetic acid. Fractions containing GCSF were pooled, concentrated in an AMICON positive pressure cell using a YM 10 membrane and dialysed for 72 h against sterile distilled water.

1.8 Preparation of DTP-dodecylsuberlhexyl-$eVB_{12}$ reagent.

Although the DTP-dodecyl-$eVB_{12}$ reagent reacts efficiently with GCSF to give a stable, well characterised complex, the material had a low IF affinity (~2–3% of native $eVB_{12}$). A complex with increased IF affinity was prepared by synthesising an extended spacer analogue of the DTP-dodecylamino-$eVB_{12}$. The synthesis of this analogue uses the same SPDP chemistry to conjugate through the cysteine of GCSF, however a longer spacer arm is attached to the $eVB_{12}$. As anticipated, this resulted in the formation of a conjugate whose IF affinity is significantly greater than that of the conjugate prepared by the reaction of GCSF with DTP-dodecyl-$eVB_{12}$ (see Table 2).

This spacer was prepared by sequential reaction of the e-carboxylate of $eVB_{12}$ with:

i) 1,6-diaminohexane and EDAC (to give 6-aminohexyl $eVB_{12}$).
ii) disuccinimidyl suberate (DSS) (to give monosuccinimidylsuberylhexyl-$eVB_{12}$).
iii) 1,12-diaminododecane (to give 12-aminododecylsuberylhexyl-$eVB_{12}$).

That is:

$$eVB_{12}CO_2H \rightarrow eVB_{12}CONH(CH)_6NH2 \rightarrow$$
$$eVB_{12}CONH(CH_2)_6NHCO(CH_2)COOSu \rightarrow$$
$$eVB_{12}CONH(CH_2)_6NHCO(CH_2)_6CONH(CH_2)_{12}NH_2$$

The resultant spacer, which is more than twice the length of aminododecyl-$eVB_{12}$, was derivatized at the terminal amino group with SPDP and coupled to GCSF by means of the protocol in the following section.

1.9 Conjugation of DTP-dodecylsuberylhexyl-$eVB_{12}$ to GCSF

A solution of the DTP-dodecylsuberlhexyl-$eVB_{12}$ (9 mg, 7 μmol) was taken up in acetic acid (100 μl) and diluted to 1 ml with water. This solution was added to 5 ml of GCSF solution (4 mg/ml, 0.5 μmol) cooled to 4 C. The reaction mixture was left for 144 h at 4 C., then worked up using the standard protocol.

1.10 Production of hydrazide derivatives of $eVB_{12}$ carboxylate

Two hydrazide derivatives of $eVB_{12}$ carboxylate were prepared for conjugation to carboxyl groups of GCSF by reaction with EDAC. The two hydrazide derivatives used, and their (shorthand) chemical structure, are:

a) hydrazido-$eVB_{12}$ (=$eVB_{12}$—$CONHNH_2$)
(b) adipyl-hydrazido-$eVB_{12}$ (=$eVB_{12}$—$CONHNHCO(CH_2)_4CONHNH_2$)

1.10i Hydrazido-$eVB_{12}$

This reagent was prepared by a two step synthesis involving the coupling of tert butyl carbazate to $eVB_{12}$ carboxylate and subsequent removal of the tBoc group to generate the free hydrazide.

$$\begin{array}{cc} H_2NNHCO_2{}^tBu & 10\% \text{ TFA/}H_2O \\ eVB_{12}CO_2H \rightarrow eVB_{12}CONHNHCO_2{}^tBu \rightarrow eVB_{12}CONHNH_2 \\ EDAC & \end{array}$$

1.10ii Adipyl-hydrazido-$eVB_{12}$

This reagent was readily prepared in one step from $eVB_{12}$ carboxylate by the addition of EDAC to a mixture of the acid and a 20-fold excess of adipylhydrazide.

$$\begin{array}{c} 20 \text{ eq. adipyl hydrazide} \\ eBV_{12}CO_2H \rightarrow eVB_{12}CONHNHCO(CH_2)_4CONHNH_2 \\ EDAC \end{array}$$

EDAC-mediated coupling of hydrazido-$eVB_{12}$ analogues to the carboxylate side-chains of GCSF proceeded more readily, and required significantly lower amounts of $eVB_{12}$ derivative and EDAC, than the corresponding conjugations of amino $eVB_{12}$ derivatives to GCSF. This is readily explainable in terms of the relative basicity of hydrazides (pKa 2.6) in comparison with amines (pKa 8–9). Thus at the pH at which the GCSF coupling takes place (4–5) a hydrazido $eVBt_{12}$ derivative will be primarily in the reactive, non-protonated form while an amino-$eVB_{12}$ derivative will be primarily in the non-reactive, protonated form.

The coupling reaction used is:

*EDAC*

$$eVB_{12}\text{—[spacer]—}CONHNH_2 + HO_2C\text{-GCSF} \rightarrow eVB_{12}\text{—[spacer]} \text{—}CONHNHCO\text{—}GCSF$$

1.11 Conjugation of hydrazido-$eVB_{12}$ to GCSF

A solution of hydrazido $eVB_{12}$ (8.9 mg, 6.5 μmol) in 5 ml of GCSF solution (4 mg/ml, 1.05 μmol) was cooled to 4 C. and an aliquot of EDAC solution (50 mg/ml, 40 μl, 10 μmol) was added. After 5 h an identical aliquot of fresh EDAC solution was added and the reaction mixture was left overnight at 4 C. Conjugate was removed from unreacted $eVB_{12}$ and other reagents by chromatography on Sephadex G-50 in 2.5% acetic acid.

1.12 Conjugation of adipylhydrazido-$eVB_{12}$ to GCSF

A solution of adipylhydrazido $eVB_{12}$ (10 mg, 6.6 μmol) in 3 ml of GCSF solution (4 mg/ml, 0.64 μmol) was cooled to 4 C. and an aliquot of EDAC solution (50 mg/ml, 40 μl, 10 μmol) was added. After 5 h a 20 μl aliquot of fresh EDAC solution (50 mg/ml, 20 μml, 5 μmol) was added and the reaction mixture was left overnight at 4 C. Conjugate was removed from unreacted $eVB_{12}$ and other reagents by chromatography on Sephadex G-50 in 2.5% acetic acid.

1.13 Preparation of poly-GCSF-HPMA-$eVB_{12}$ a complex.

Two N-(2-hydroxypropyl)methacrylamide (HPMA) copolymers can be synthesized as polymer backbones for the incorporation and derivatization with GCSF and $eVB_{12}$. A non-biodegradable polymer backbone (HPMA-GG) can be synthesized by the free radical copolymerization of HPMA with N-methacryloylglycylglycine p-nitrophenyl ester. A biodegradable polymer (HPMA-FALG) can be synthesized by the free radical copolymerization of HPMA with N-methacryloylgly cylphenylalanylleucylglycine p-nitrophenol ester by the method of Regmanova and coworkers [Regmanova, P, Obereigner, B and Kopecek, J, 1981 Makromol Chem 182:1899–1915]. In order to incorporate GCSF and $eVB_{12}$ onto the polymers, the polymers are initially reacted with a ten molar excess of a mixture of aminododecyl-$eVB_{12}$ and dithiopyridyldodecylsuberyl-hexylamine (1:10 mole:mole) overnight. Unreacted nitrophenyl esters are subjected to aminolysis by the addition of 1-amino-2-propanol. The modified polymers are purified by chromatography on Sepharose 6B. A solution of the dithiopyridyldodecylsuberylhexyl modified $eVB_{12}$-substituted polymers is dissolved in 2.5% acetic acid and reacted with GCSF. The reaction mixture is left for 144 h at 4 C., afterwhich the GCSFe$VB_{12}$-substituted polymers can be purified by chromatography on Sepharose 6B.

Part 2: $eVB_{12}$-EPO complexes

Three classes of $eVB_{12}$-EPO complexes were prepared:

(a) Conjugated via an amide linkage, formed by EDAC-mediated coupling of an amino $eVB_{12}$ derivative to the C-terminus of EPO, the carboxylate side chains of the Asp/Glu residues of EPO or the carboxylate groups of the sialic acid residues of the carbohydrate portion of EPO.

(b) Conjugated via an acyl hydrazide linkage, formed by EDAC-mediated coupling of a hydrazido-$eVB_{12}$ derivative to the carboxylate side chains of the Asp/Glu residues of EPO or the carboxylate groups of the sialic acid residues of the carbohydrate portion of EPO.

(c) Conjugated via a hydrazone linkage between a hydrazido-$eVB_{12}$ derivative and an aldehyde group generated by periodate oxidation of the carbohydrate residues of EPO.

2.1 Conjugation of 2-aminoethyl-$eVB_{12}$ to EPO

A mixture of 2-aminoethyl-$eVB_{12}$ (8 mg, 5.7 μmol) and EPO (27 mg/ml, 200 μl, 0.18 μmol) was cooled to 4 C. and an aliquot of EDAC solution (10 mg/ml, 100 μl, 5 μmol) was added. The reaction mixture was left for 64 h at 4 C. and finally purified by size-exclusion chromatography on a Superdex-75 column. Elution with a buffer consisting of Tris (pH 7.5, 10 mM; NaCl, 100 mM) afforded the purified EPO-$eVB_{12}$ complex.

2.2 Conjugation of cystaminyl-$eVB_{12}$ to EPO

A mixture of 6-amino-3,4-dithiahexylamide-$eVB_{12}$ (12 mg, 8.1 μmol) and EPO (13.5 mg/ml, 500 μl, 0.23 μmol) was cooled to 4 C. and an aliquot of EDAC solution (10 mg/ml, 250 μl, 13 μmol) was added. The reaction mixture was left for 48 h at 4 C. and was finally purified by size-exclusion chromatography on a Sephadex G-75 column. Elution with a buffer consisting of Tris (pH 7.5, 10 mM)/NaCl (100 mM) afforded the purified EPO-eVB$_{12}$ complex 2.3 EDAC-mediated conjugation of hydrazido-eVB$_{12}$ to EPO A solution of hydrazido VB$_{12}$ (10 mg, 7.3 μmol) in 7 ml of EPO solution (2.6 mg/ml, 0.6 μmol) was cooled to 4 C. and an aliquot of EDAC solution (20 mg/ml, 50 μl, 5 μmol) was added. After 5 h a second aliquot of fresh EDAC solution (10 mg/ml, 25 μl, 1.3 μmol) was added and the reaction mixture was left overnight at 4 C. The conjugate was purified by size-exclusion chromatography on a G-50 column. Elution with a buffer consisting of Tris (pH 7.5, 10 mM; NaCl, 100 mM) afforded the purified EPO-eVB$_{12}$ complex.

2.4 EDAC-mediated conjugation of adipyl-hydrazido-eVB$_{12}$ to EPO

A solution of adipyl-hydrazido-eVB$_{12}$ ( 11 mg, 7.3 μmol) in 4 ml of EPO solution (2.6 mg/ml, 0.35 μmol) was cooled to 4 C. and an aliquot of EDAC solution (10 mg/ml, 100 μl, 5 μmol) was added. The reaction mixture was left overnight at 4 C. The conjugate was purified by size-exclusion chromatography on a G-50 column. Elution with a buffer consisting of Tris (pH 7.5, 10 mM)/NaCl (100 mM) afforded the purified EPO-eVB$_{12}$ complex.

2.5 Periodate mediated conjugation of hydrazido-eVB$_{12}$ to EPO

An aqueous solution of EPO (6.4 mg/ml, 1.56 ml, 0.33 μmol) was cooled to 4 C. and freshly prepared sodium periodate solution (25 mM, 360 μl) was added. The solution was left to stir gently for fifteen minutes at 4 C. and the excess periodate was quenched by the addition of ethylene glycol (5 μl). The solution was dialyzed overnight against 3 l of pH 5.6, 10 mM NaOAc buffer. A solution of hydrazido-eVB$_{12}$ (7.5 mg, 5 μmol) in distilled water (200 μl) was added to the oxidised EPO solution and the reaction mixture was left for 7 h at 4 C. The conjugate was separated from unreacted hydrazide by SEC on G-75 Sephadex. Elution with a buffer consisting of Tris (pH 7.5/10 mMl)/NaCl (100 mM) afforded the purified EPO-eVB$_{12}$ complex.

2.6 Preparation of poly-EPO-HPMA-eVB$_{12}$

Two N-(2-hydroxypropyl)methacrylamide (HPMA) copolymers can be synthesized as polymer backbones for the incorporation and derivatization with EPO and VB$_{12}$. A nonbiodegradable polymer backbone (HPMA-GG) is synthesized by the free radical copolymerization of HPMA with N-methacryloylglycylglycine p-nitrophenyl ester. A biodegradable polymer (HPMA-GFAG) is synthesized by the free radical copolymerization of HPMA with N-methacryloylglycyl-phenylalanylleucylglycine p-nitrophenol ester by the method of Rejmanova and coworkers [Rejmanova, P, Obereigner, B and Kopecek J, 1981 Makromol Chem 182:1899–1915]. In order to incorporate EPO and eVB$_{12}$ onto the polymers, the polymers are reacted with a ten molar excess of a mixture of aminododecyl-eVB$_{12}$ and 6-( 3-acylhydrazidylpropionamido)-1-amino-3,4-dithiahexane(1:10mole:mole)overnight. Unreacted nitrophenyl esters are subjected to aminolysis by the addition of 1-amino-2-propanol. The modified polymers are purified by chromatography on Sepharose 6B. EPO is covalently linked to the 6-(3-acylhydrazidylpropionamido)-1-amino-3,4-dithiahexane modified eVB$_{12}$-substituted polymers by the addition of EDAC. The reaction mixture is left for 18 h at 4 C., afterwhich the EPO-eVB$_{12}$-substituted polymers are purified by chromatography on Sepharose 6B.

Example 3:

The diradical spacer may be selected with a suitable length and functionality to optimize the intrinsic factor (IF) affinity of the resulting GCSF or EPO eVB$_{12}$ complex. As examples of this, the following table shows the result of altering the length and functionality of the spacer for various complexes and VB$_{12}$ derivatives.

The IF affinity of the various eVB$_{12}$ analogues and complexes referred to in the Examples are shown in Table 2. In particular, there is significant increase in IF affinity between the GCSF-dithiopropionamido[12-aminododecylamido]-eVB$_{12}$ (preparated in section 1.7) and the GCSF-dithiopropionamido[12-aminododecyl-subeyl-hexylamido]-eVB$_{12}$ (prepared in section 1.9). This increase in IF affinity presumably results from the increase in length of the spacer arm in the latter complex.

TABLE 2

Relative Intrinsic Factor affinity of VB$_{12}$ analogues and complexes

| eVB$_{12}$ Analogue or complex | IF Affinity |
| --- | --- |
| eVB$_{12}$carboxylate | 35% |
| 2-aminoethylamido-eVB$_{12}$ | 48% |
| 6-aminohexylamido-eVB$_{12}$ | 91% |
| 12-aminododecylamido-eVB$_{12}$ | 74% |
| 12-aminododecyl-suberyl-hexylamido-eVB$_{12}$ | 82% |
| dithlopropionamido[2-aminoethylamido]-eVB$_{12}$ | 6% |
| dithiopropionamido[6-aminohexylamido]-eVB$_{12}$ | 7% |
| dithioproplonamido[6-aminohexylamido]-eVB$_{12}$ | 11% |
| GCSF-dithioproplonamido[12-aminododecylamido]-eVB$_{12}$ | 3% |
| GCSF-diothloproplonamido12-aminododecyl-suberyl-hexylamido-eVB$_{12}$ | 28% |
| hydrazidyl-eVB$_{12}$ | 100% |
| adipyldihydrazidyl-eVB$_{12}$ | 44% |
| GCSF-acylhydrazidyl-eVB$_{12}$ | 10% |
| GCSF-acyl[adipyldihydrazidyl]-eVB$_{12}$ | 7% |
| EPO-acylhydrazidyl-eVB$_{12}$ | 6% |
| EPO-acyl[adipyldlhydrazidyl]-eVB$_{12}$ | 11% |

IF Affinity is expressed as a percentage of the affinity of the eVB$_{12}$ derivative relative to native, unmodified VB$_{12}$.

We claim:

1. A covalent conjugate comprising erythropoietin (EPO) and vitamin B$_{12}$ or an analogue of vitamin B$_{12}$, said EPO being covalently bound to said vitamin B$_{12}$ or analogue of vitamin B$_{12}$ by a diradical spacer such that said conjugate binds to intrinsic factor with high affinity and maintains erythropoietin (EPO) bioactivity.

2. A complex according to claim 1, wherein said diradical spacer is covalently linked to erythropoietin (EPO) through: an amide linkage; an acyl hydrazide linkage; an imine linkage; or a hydrazone linkage.

3. A covalent conjugate according to claim 1, wherein said analogue of vitamin B$_{12}$ is an analogue where the corrin ring is substituted with any of a group of corrin ring constituents selected from the group consisting of: cyanocobalimin, aquocobalimin, adenosylcobalimin, methylcobalimin, hydroxycobalimin, and their desdimethyl, monoethylamide, and methylamide derivatives; alkyl cobalimins in which the alkyl chain is linked to the corrin nucleus by a direct cobalt-carbon covalent bond; chlorocobalimin, sulfitocobalimin, nitrocobalimin, thiocyanatocobalimin; the anilide, ethylamide, propionamide, monocarboxylic and dicarboxylic acid derivatives of vitamin B$_{12}$ and its analogues; the monocarboxylic, dicarboxylic, and tricarboxylic acid derivatives and the propionamide derivatives of the "e" isomer of monocarboxy vitamin B$_{12}$; and analogues of vitamin B$_{12}$ in which the cobalt is replaced by zinc or nickel.

4. A covalent conjugate according to claim 1, wherein said erythropoietin (EPO) is covalently bound to a pharmaceutically acceptable polymer.

5. A covalent conjugate according to claim 4, wherein said pharmaceutically acceptable polymer is biodegradable within the human or animal body.

6. A covalent conjugate according to claim 1 of the formula:

$$V-X-A-Y-Z$$

wherein,

V is vitamin $B_{12}$ or an analogue of vitamin $B_{12}$ or derivative, bonded to X either through a carboxylate group pendant to the corrin nucleus of vitamin $B_{12}$ or through the central cobalt atom or to a functional group introduced onto the vitamin $B_{12}$ molecule, X is selected from: —NHNH—, —NH—, —O—, S—, —SS— and —CH$_2$—, and A is an optionally substituted, saturated or unsaturated, branched or linear, $C_{1-50}$ alkylene, cycloalkylene or aromatic group, optionally with one or more carbons within the linear chain being replaced with N, O or S, and wherein the optional substituents are selected from carbonyl, carboxy, hydroxy, amino and other groups, and Y is the covalent linkage between A and Z where Y is selected from —NHCO—, —CONH—, —CONHNHCO—, —N=N—, —N=CH—, —NHCH$_2$—, —NHN=CH—, —NHNHCH$_2$—, —SS—, —SCH$_2$—, —CH$_2$S—, —NHCRNH—, (R is O, S or NH$_2$), —COO—, —OCO—, and Z is erythropoietin (EPO).

7. A covalent conjugate according to claim 1, wherein said analogue of vitamin $B_{12}$ is selected from cyano-cobalamin (CN-Cbl), aquocobalamin, adenosylcobalamin, methylcobalamin, hydroxycobalamin, 5-methoxybenzyl(cyano)cobalamin {(5-MeOBz)CN-Cbl}; the desdimethyl, monoethylamide and the methylamide derivatives of these; alkyl cobalamins in which the alkyl chain of said alkyl cobalimins is linked to the corrin nucleus by a direct cobalt-carbon covalent bond; chlorocobalamin, sulfitocobalamin, nitrocobalamin, thiocyanatocobalamin, benzimidazole(cyano)cobalamin derivatives including 5,6-dichlorobenzimidazole, 5-hydroxybenzimidazole, trimethylbenzimidazole; adenosylcyanocobalamin {(Ade)CN-Cbl}, cobalamin lactone, cobalamin lactam; the anilide, ethylamide, monocarboxylic and dicarboxylic acid derivatives of vitamin $B_{12}$ or its analogues; the mono-, di- and tricarboxylic acid derivatives or the propionamide derivatives of the "e" isomer of monocarboxy vitamin $B_{12}$; and analogues of vitamin $B_{12}$, in which the cobalt is replaced by zinc or nickel.

8. A covalent conjugate according to claim 4, wherein the polymer is selected from dextran, inulin, cellulose, starch and derivatives thereof, chondroitan sulfate, poly{N-α-(2-hydroxypropyl)-methacrylamide} and derivatives thereof, styrene-maleic anhydride copolymer, divinylether-maleic anhydride copolymer, polylysine, poly(glutamic acid), poly-(hydroxypropyl glutamine), poly(lactic acid), water soluble polyurethanes formed by covalent linkage of PEG with lysine or other amino acids and branched chain polypeptides.

9. A pharmaceutical composition which comprises a covalent conjugate according to claims 1, 2, 3, 4, 5, or 6–8, in association with a pharmaceutically acceptable carrier or excipient.

* * * * *